US007614168B1

(12) United States Patent
Zummer et al.

(10) Patent No.: US 7,614,168 B1
(45) Date of Patent: Nov. 10, 2009

(54) MASSAGING INNERSOLE

(76) Inventors: David Zummer, 42-30 Marathon Pkwy., Little Neck, NY (US) 11363; Glenn Zummer, 42-30 Marathon Pkwy., Little Neck, NY (US) 11363; Brian Hendrickson, 30145 North Rd., Peconic, NY (US) 11958

( * ) Notice: Subject to any disclaimer, the term of this patent is extended or adjusted under 35 U.S.C. 154(b) by 538 days.

(21) Appl. No.: 11/657,998

(22) Filed: Jan. 25, 2007

Related U.S. Application Data

(60) Provisional application No. 60/763,493, filed on Jan. 30, 2006, provisional application No. 60/802,547, filed on May 22, 2006.

(51) Int. Cl.
*A61F 5/14* (2006.01)

(52) U.S. Cl. .......................................... 36/141; 36/29

(58) Field of Classification Search .................. 36/141, 36/29, 43, 44
See application file for complete search history.

(56) References Cited

U.S. PATENT DOCUMENTS

| | | | | |
|---|---|---|---|---|
| 3,731,674 | A | 5/1973 | Parvin | |
| 4,802,463 | A | 2/1989 | Rojas | |
| 5,113,850 | A | 5/1992 | Larremore et al. | |
| 5,592,759 | A | 1/1997 | Cox | |
| 5,836,899 | A | 11/1998 | Reilly | |
| 5,913,838 | A | 6/1999 | Reilly | |
| 6,234,987 | B1 | 5/2001 | Chen | |
| 6,282,815 | B1 | 9/2001 | Caston | |
| 6,464,654 | B1 | 10/2002 | Montgomery et al. | |
| 7,231,730 | B1 * | 6/2007 | Ryan et al. | 36/141 |
| 7,347,831 | B2 * | 3/2008 | Chiu | 601/15 |
| 2002/0095104 | A1 | 7/2002 | Chen | |
| 2005/0126049 | A1 | 6/2005 | Koenig | |
| 2005/0172515 | A1 | 8/2005 | Ungari | |
| 2006/0030799 | A1 | 2/2006 | Adkins et al. | |
| 2006/0036197 | A1 | 2/2006 | Liu et al. | |
| 2006/0213091 | A1 * | 9/2006 | Ometto et al. | 36/141 |
| 2007/0256333 | A1 * | 11/2007 | Wolf | 36/141 |
| 2008/0132811 | A1 * | 6/2008 | Yang et al. | 601/30 |

* cited by examiner

*Primary Examiner*—Marie Patterson
(74) *Attorney, Agent, or Firm*—Collard & Roe, P.C.

(57) ABSTRACT

A foot massaging device includes a flexible innersole for removably inserting in an article of footwear. A thin layer of material is disposed over an upper surface of the innersole. A rechargeable battery disposed in the innersole is coupled to a switch and a charging port. A massaging effect on the bottom of a user's foot is produced by means of reciprocating rollers, inflatable bladders and/or pivoting rocker members.

15 Claims, 9 Drawing Sheets

MASSAGING INNERSOLE

CROSS REFERENCE TO RELATED APPLICATIONS

This application claims the benefit of U.S. Provisional Application No. 60/763,493 filed on Jan. 30, 2006 and U.S. Provisional Application 60/802,547 filed on May 22, 2006.

BACKGROUND OF THE INVENTION

1. Field of the Invention

The invention relates to foot massaging devices for producing a massaging effect on the bottom of a user's foot. More particularly, the invention relates to battery-powered massaging devices which can be removably inserted into an article of footwear.

2. The Prior Art

The following references, the disclosures of which are hereby incorporated herein by reference, relate to devices for providing a vibratory massage to a person's foot or feet: U.S. Pat. Nos. 5,913,838 and 5,836,899 to Reilly; U.S. Patent Application Publication No. 2005/0126049 to Koenig; U.S. Pat. No. 6,464,654 to Montgomery et al.; U.S. Pat. No. 5,592,759 to Cox; U.S. Pat. No. 5,113,850 to Larremore et al.; U.S. Pat. No. 4,802,463 to Rojas; U.S. Pat. No. 3,731,674 to Parvin; and U.S. Patent Application Publication No. 2002/0095104 to Chen.

U.S. Pat. No. 6,234,987 to Chen and U.S. Patent Application Publication No. 2005/0172515 to Ungari, the disclosures of which are hereby incorporated herein by reference, show footwear devices which require magnets or magnetic fields for operation.

U.S. Patent Application Publication No. 2006/0036197 to Liu et al., the disclosure of which is hereby incorporated herein by reference, shows an electro-stimulation physiotherapy shoe for stimulating acupuncture points at the soles of the feet with low and medium frequency electric waves.

U.S. Patent Application Publication No. 2006/0030799 to Adkins et al. the disclosure of which is hereby incorporated herein by reference, shows a foot massaging device based on reflexology concepts. The device includes an inflatable air bladder which inflates and deflates to provide a massage to the top of the foot.

U.S. Pat. No. 6,282,815 to Caston, the disclosure of which is hereby incorporated herein by reference, shows a shoe sole having fluid-filled tubes along its perimeter for cushioning the various part of the foot. The force of a wearer's weight coming down on the shoe as the wearer runs or walks displaces the fluid to cushion the foot and adjustable pressure valves permit fluid to flow between tubes in only one direction and allow control of the shock absorption properties of the shoe.

SUMMARY OF THE INVENTION

Foot massaging devices for producing a massaging effect on the bottom of a user's foot are provided. In a first aspect, a foot massaging device includes an innersole for removably inserting in an article of footwear. The innersole includes a flexible material. A thin layer of material is disposed over an upper surface of the innersole. A motor is disposed in a cavity provided in the innersole and a rechargeable battery for powering the motor is disposed in the innersole and coupled to the motor. A switch is coupled to the rechargeable battery and to the motor for selectively powering the motor. A charging port is coupled to the rechargeable battery for coupling to a charger. A cam is coupled to the motor and a plurality of rails are coupled to the cam. The rails are movable within channels provided in the innersole. A plurality of spaced-apart rollers are disposed on each of the rails. When the motor is powered, the cam is rotated causing the rails to move in a reciprocating manner, moving the rollers back and forth to produce a massaging effect on the bottom of a user's foot.

In a second aspect, a foot massaging device includes an innersole for removably inserting in an article of footwear. The innersole includes a flexible material. A thin layer of material is disposed over an upper surface of the innersole. A pump is disposed in a cavity provided in the innersole and a rechargeable battery for powering the pump is disposed in the innersole and coupled to the pump. A switch is coupled to the rechargeable battery and to the pump for selectively powering the pump. A charging port is coupled to the rechargeable battery for coupling to a charger. Inflatable bladders are disposed within the innersole and coupled to the pump. When the pump is powered, the inflatable bladders are inflated to produce a massaging effect on the bottom of a user's foot.

In a third aspect, a foot massaging device includes an innersole for removably inserting in an article of footwear. The innersole includes a flexible material. A thin layer of material is disposed over an upper surface of the innersole. Expanding and contracting bladders are disposed in the innersole and artificial muscles are disposed in cavities provided in the bladders. The artificial muscles expand and contract in response to an electrical current applied to the artificial muscles. A rechargeable battery for applying the electrical current to the artificial muscles is disposed in the innersole and coupled to the artificial muscles. A switch is coupled to the rechargeable battery and to the artificial muscles for selectively applying the electrical current to the artificial muscles. A charging port is coupled to the rechargeable battery for coupling to a charger. When the electrical current is applied to the artificial muscle, the artificial muscle expands and contracts within an associated bladder to produce a massaging effect on the bottom of a user's foot.

In a fourth aspect, a foot massaging device includes an innersole for removably inserting in an article of footwear. The innersole includes a flexible material. A thin layer of material is disposed over an upper surface of the innersole. A motor is disposed in a cavity provided in the innersole and a rechargeable battery for powering the motor is disposed in the innersole and coupled to the motor. A switch is coupled to the rechargeable battery and to the motor for selectively powering the motor. A charging port is coupled to the rechargeable battery for coupling to a charger. A cam is coupled to the motor and a plurality of rails are coupled to the cam. The rails are movable within channels provided in the innersole. Each of the rails include a plurality of teeth. Spaced-apart pivoting rocker members are disposed over the rails and each of the rocker members have a lever for engaging at least one of the teeth on a rail. When the motor is powered, the cam is rotated causing the rails to move in a reciprocating manner, and the teeth contact the levers causing the rocker members to pivot, producing a massaging effect on the bottom of a user's foot.

An advantage of a foot massaging device according to an embodiment of the invention is that the device can be easily and readily inserted and removed from a wide variety of footwear types and styles. A further advantage of a foot massaging device according to an embodiment of the invention is that a dual charging device may be provided which allows for the charging of foot massaging devices inserted into each of a pair of shoes or other footwear using a single charging device and without having to remove the foot massaging devices from the respective footwear.

BRIEF DESCRIPTION OF THE DRAWINGS

Other benefits and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENTS

Figure 1A:
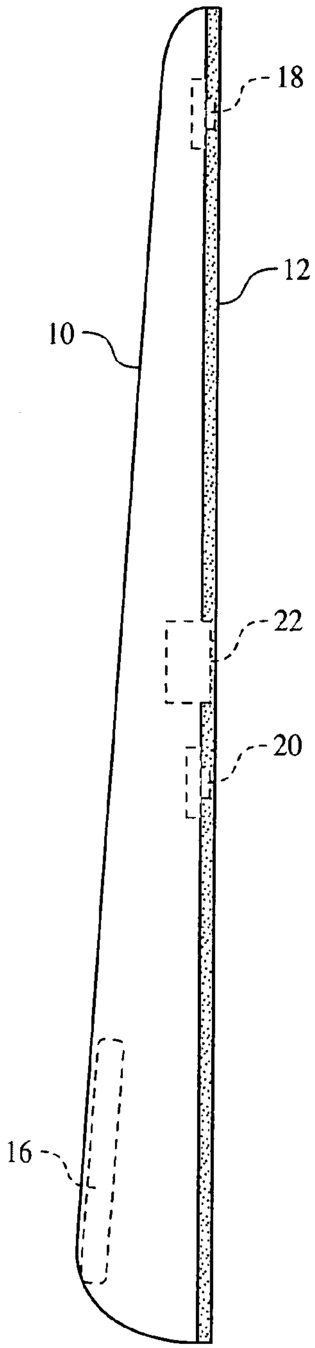
FIG. 1A shows a side view of a foot massaging device according to an embodiment of the invention.
Figure 1B:
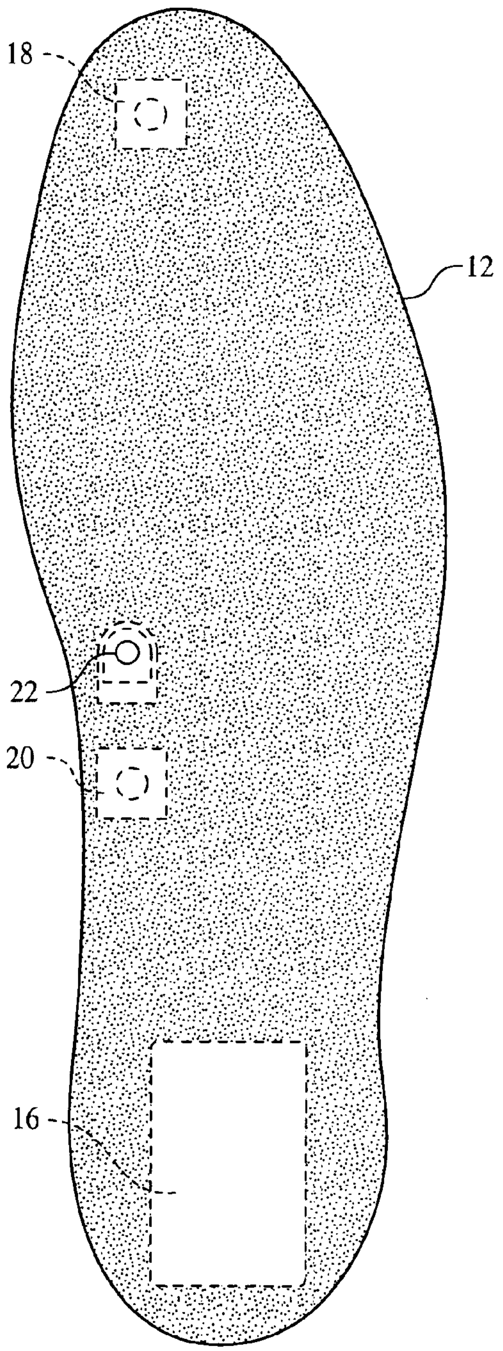
FIG. 1B shows a top view of the embodiment shown in FIG. 1A.
Figure 1C:
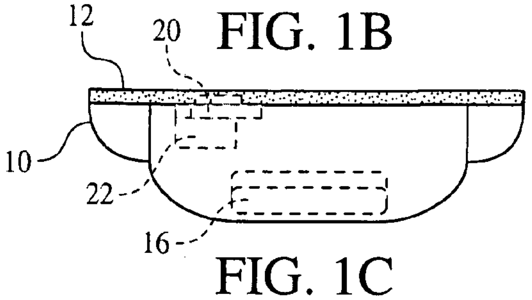
FIG. 1C shows a rear view of the embodiment shown in FIGS. 1A and 1B.
Figure 2A:
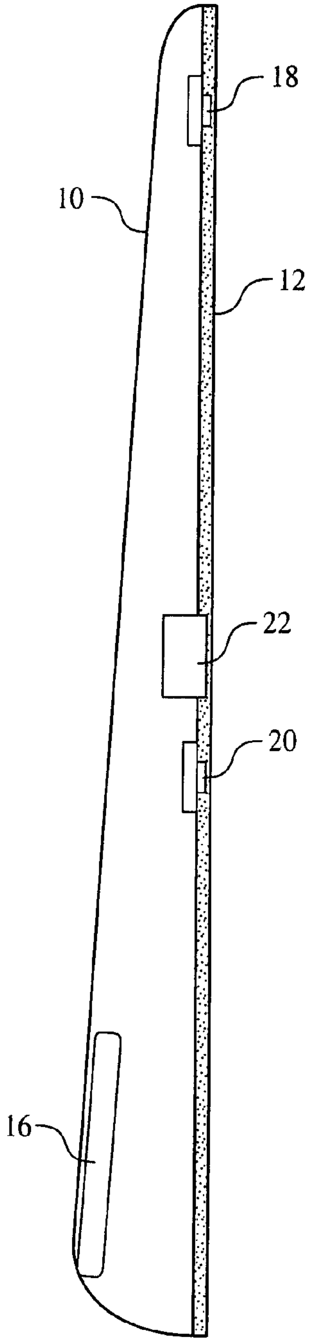
FIG. 2A shows a side view of a foot massaging device according to another embodiment of the invention.
Figure 2B:
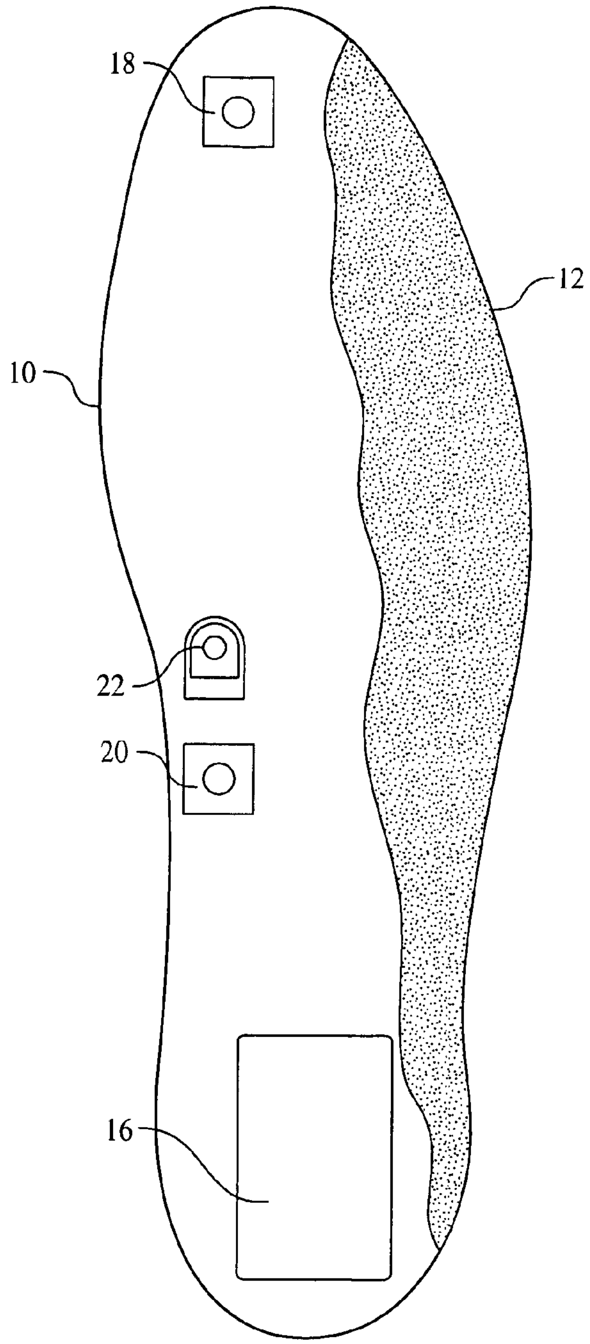
FIG. 2B shows a top view of the embodiment shown in FIG. 2A.
Figure 2C:
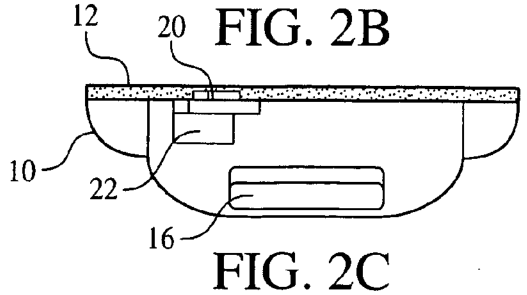
FIG. 2C shows a rear view of the embodiment shown in FIGS. 2A and 2B.
Figure 3A:
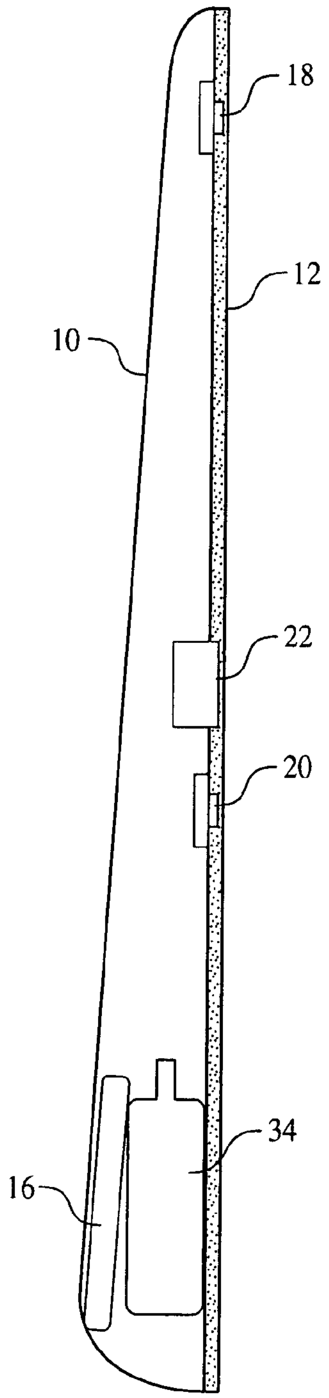
FIG. 3A shows a side view of a foot massaging device according to another embodiment of the invention.
Figure 3B:
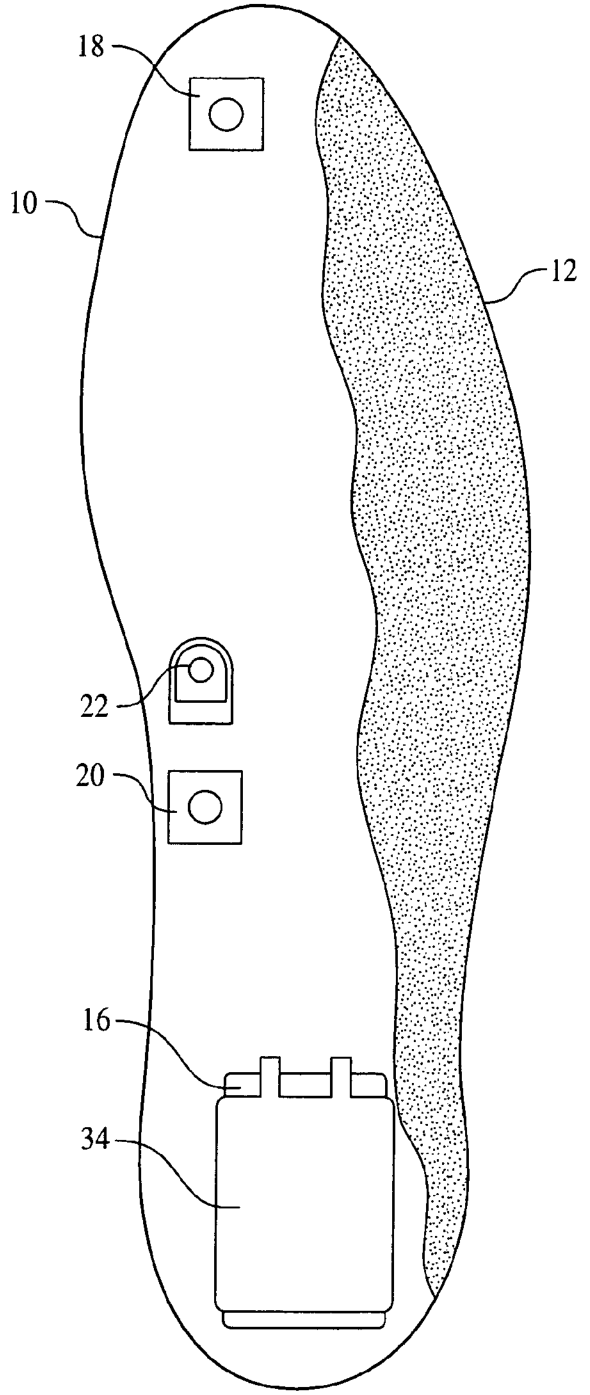
FIG. 3B shows a top view of the embodiment shown in FIG. 3A.
Figure 3C:
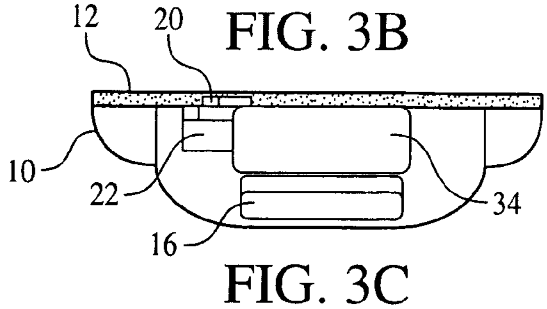
FIG. 3C shows a rear view of the embodiment shown in FIGS. 3A and 3B.

Referring now in detail to the drawings and in particular, FIGS. 1A, 1B and 1C show a foot massaging device according to an embodiment of the invention. The device includes an innersole 10 which is sized and shaped to be removably inserted into a article of footwear, for example a shoe, boot, sneaker, or the like. The innersole 10 may be formed from a flexible material. For example, the innersole 10 may include a plastic, elastomer and/or rubber material.

Figure 6A:
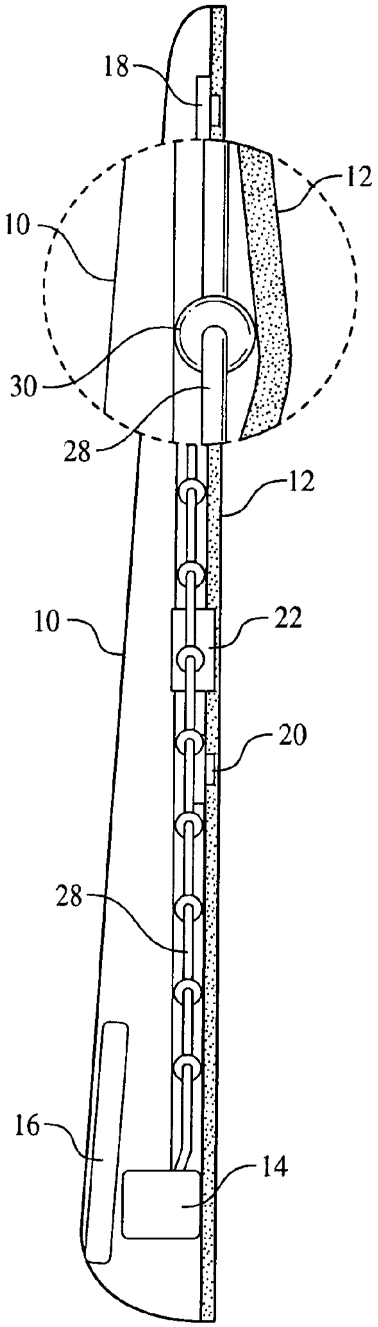
FIG. 6A shows a side view of a foot massaging device according to another embodiment of the invention.
Figure 7A:
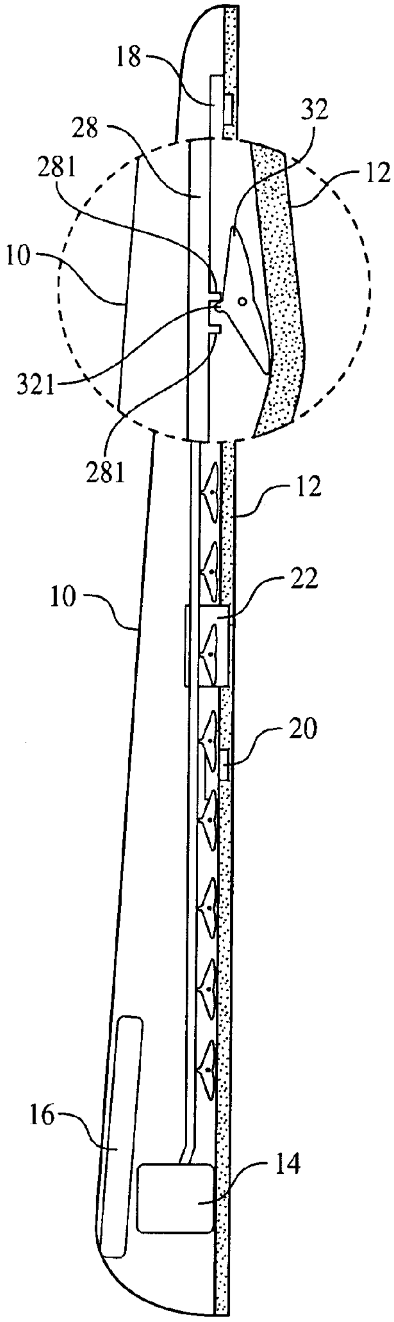
FIG. 7A shows a side view of a foot massaging device according to another embodiment of the invention.

A thin layer of material 12 is disposed over a top surface of the innersole 10 as shown. Thin layer of material 12 may cover a portion of or substantially all of the top surface of innersole 10. Thus, when innersole 10 is inserted in an article of footwear, thin layer 12 is positioned adjacent to a bottom surface of the wearer's foot and provides a surface which is comfortable to a wearer of the device when worn. Layer 12 may comprise, for example, a thin cushioning layer formed from a foam-type material or any other suitable material for providing a comfortable surface for the foot of a user of the foot massaging device. Moreover, as shown in the detailed portions of FIGS. 6A and 7A, thin layer of material 12 may be adapted and/or configured to be displaced when acted on by moving elements of the massaging device as described in detail herein.

Figure 6B:
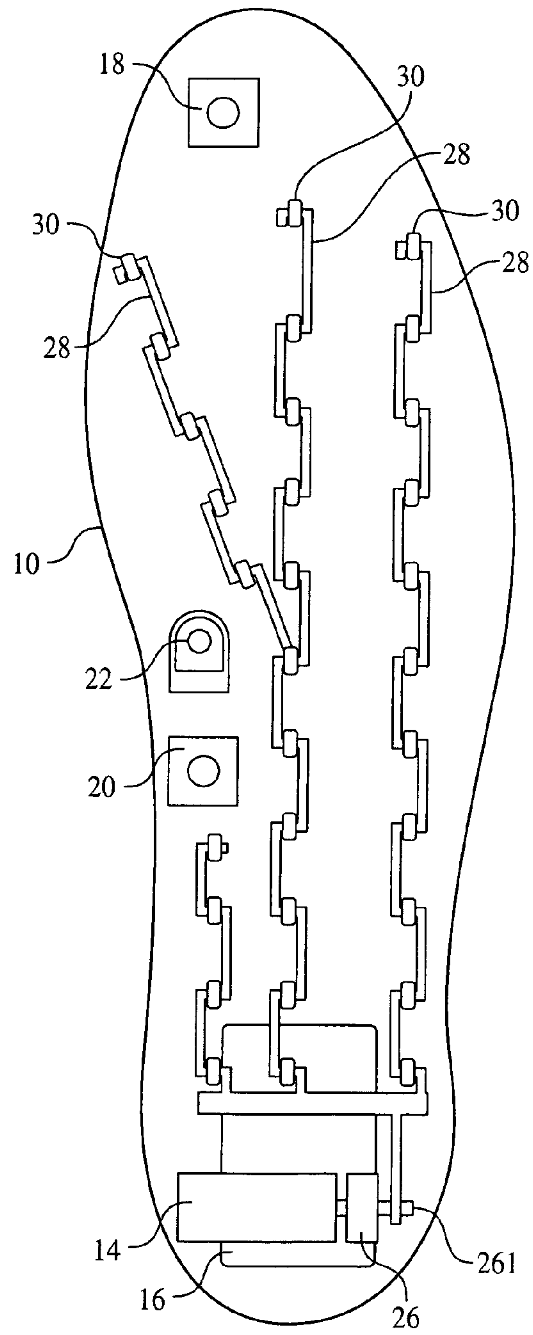
FIG. 6B shows a top view of the embodiment shown in FIG. 6A.
Figure 6C:
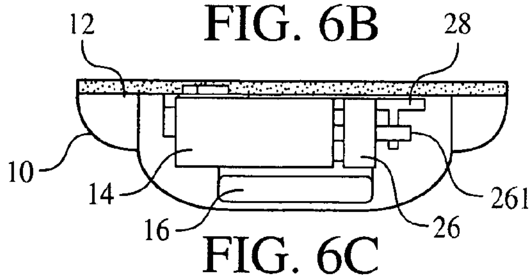
FIG. 6C shows a rear view of the embodiment shown in FIGS. 6A and 6B.
Figure 7B:
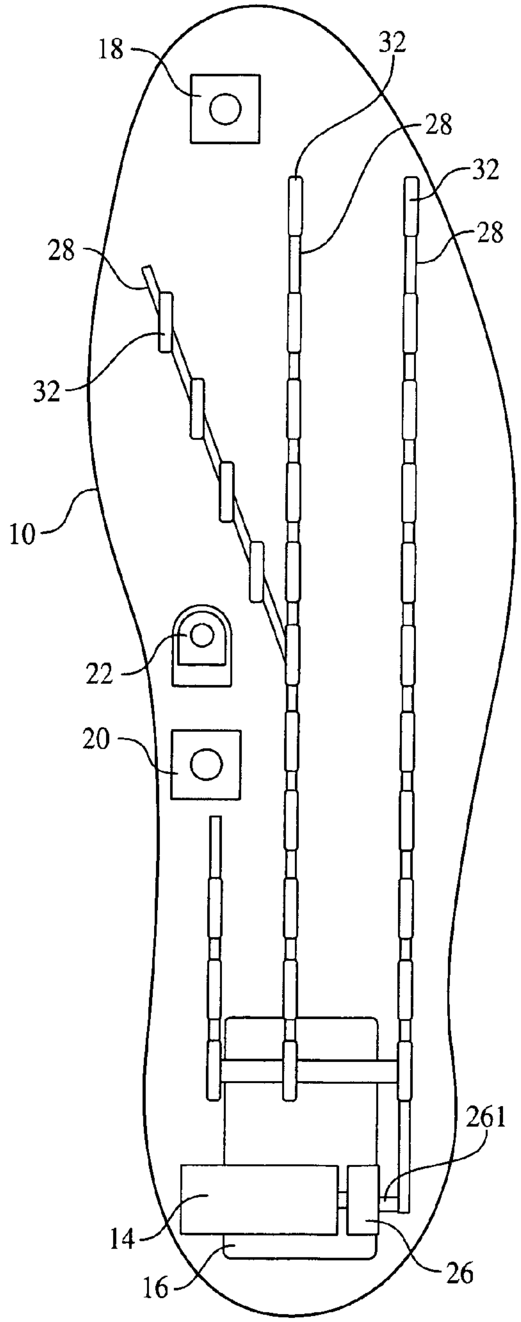
FIG. 7B shows a top view of the embodiment shown in FIG. 7A.
Figure 7C:
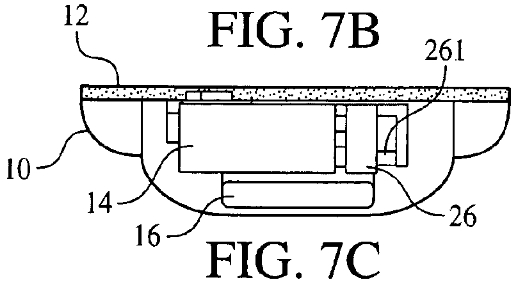
FIG. 7C shows a rear view of the embodiment shown in FIGS. 7A and 7B.

As shown in FIGS. 6 and 7, a foot massaging device according to embodiments of the invention may include a motor 14. Motor 14 is preferably an electric motor having a small profile so that it may be disposed within innersole 10. Motor 14 may be disposed within a cavity provided in innersole 10. Preferably, motor 14 is powered by a rechargeable battery 16. Rechargeable battery 16 is coupled to motor 14, for example with appropriate wiring or other electrical connections and rechargeable battery 16 is disposed in innersole 10. Preferably, rechargeable battery 16 also has a slim profile such that rechargeable battery 16 and motor 14 may be disposed within innersole 10 and innersole 10 can be inserted into an article of footwear without being prohibitively large in thickness or weight.

One or more switches 18, 20 are coupled to rechargeable battery 16 and motor 14 for selectively powering the motor. Appropriate wiring or other electrical connections may be used to couple switches 18, 20 to battery 16 and motor 14. Preferably, a switch 18 is positioned on an upper front surface of innersole 10 for actuating with a user's big toe when innersole 10 is disposed in the article of footwear. For example, switch 18 may include a plunger or similar mechanism which can be depressed by a user pushing down once on switch 18 with a toe to actuate motor 14 and pushing down again on switch 18 with a toe to disengage motor 14. One or more additional switches 20 may also be provided. For example switch 20 may comprise an override switch for disabling switch 18 such that the massaging device is not turned on inadvertently by pressure imparted on switch 18 when a user is walking or running and the user does not desire the massaging action to be activated.

Figure 9:
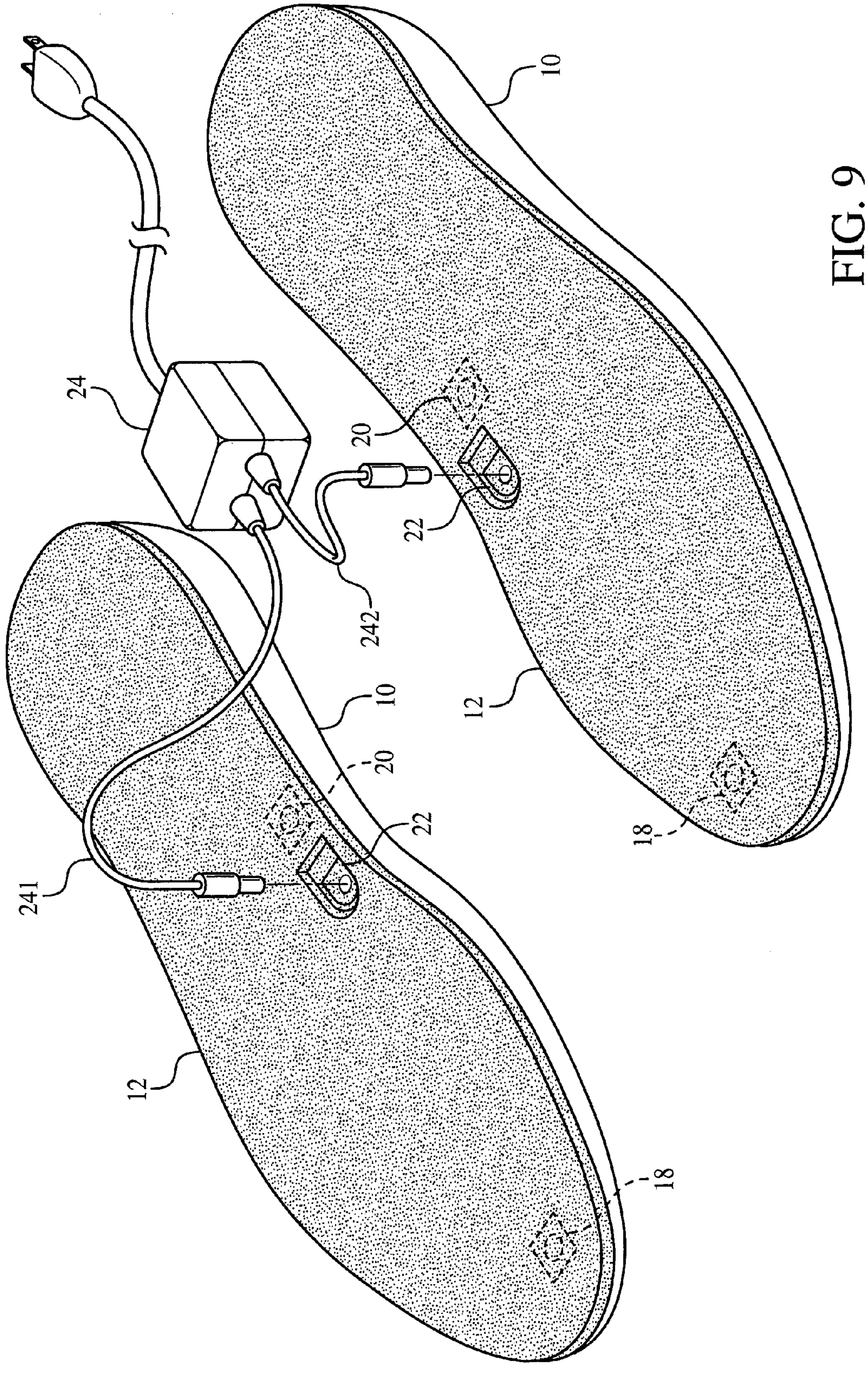
FIG. 9 shows a perspective view of a foot massaging device including a charger according to an embodiment of the invention.

A charging port 22 is coupled to the rechargeable battery 16 for coupling to a charger 24 for charging the rechargeable battery 16. Charging port 22 may be coupled to battery 16 with appropriate wiring or other electrical connections and may include an opening adapted to receive a corresponding plug portion of charger 24. As shown in FIG. 9, charger 24 is preferably adapted to be connected to an AC power supply, for example a conventional wall outlet. Charger 24 may comprise two leads 241, 242 of sufficient length for simultaneously charging a pair of the foot massage devices while each of the pair of the foot massage devices is disposed in a respective article of footwear belonging to a pair of footwear. This feature allows for the charging of foot massaging devices inserted into each of a pair of shoes or other footwear using a single charging device and without having to remove the foot massaging devices from the respective footwear.

A cam 26 is coupled to motor 14. Cam 26 may comprise a rotating, eccentric shaped member for translating the rotational motion of motor 14 to reciprocating linear motion.

As shown, for example in FIG. 6, a plurality of rails 28 are coupled to cam 26. Cam 26 may include a protruding member or peg 261 for coupling cam 26 to rails 28. Rails 28 are movable within one or more channels provided in innersole 10. Preferably, a number of rails 28 are arranged spaced apart across a width of innersole 10 to provide an effective massaging action over various portions of a user's foot.

A plurality of spaced-apart rollers 30 are disposed on each rails 28. Rollers 30 may have a rounded surface which provides a desirable massaging effect when moved over the foot of a person using the device. As shown in the detail portion of FIG. 6A, rollers 30 may displace thin layer 12 as the rollers 30 are moved back and forth with the movement of rails 28.

When motor 14 is powered, cam 26 is rotated causing the plurality of rails 28 to move in a reciprocating manner, moving the plurality of rollers 30 back and forth to produce a massaging effect on the bottom of a user's foot.

FIG. 7 shows an alternate embodiment of a foot massaging device according to the invention. In this embodiment, plurality of rails 28 include a plurality of teeth 281. Teeth 281 may extend upwardly from each of rails 28 and are spaced along rail 28 at predetermined locations.

A plurality of spaced-apart pivoting rocker members 32 are disposed over each of rails 28. Rocker members 32 include a lever 321 for engaging at least one of the teeth 281 on rails 28. Rocker members 32 may pivot about a stationary bearing member or shaft disposed in inner sole 10. As shown in the detail portion of FIG. 7A, rocker members 32 may displace thin layer 12 as the rocker members 32 are moved back and forth with the movement of rails 28. Preferably, each rail 28 includes two teeth 281 corresponding to each respective rocker member 32, wherein the teeth 281 are spaced apart such that one tooth pivots the rocker member 32 in a clockwise direction as rail 28 moves in a first direction and a first tooth contacts the lever 321 and another tooth pivots the rocker member 32 in a counterclockwise direction as rail 28 moves in a second direction and a second tooth contacts the lever 321.

When motor 14 is powered, cam 26 is rotated causing the plurality of rails 28 to move in a reciprocating manner, and teeth 281 contact levers 321 causing said plurality of rocker members 32 to pivot, producing a massaging effect on the bottom of a user's foot.

Figure 4A:
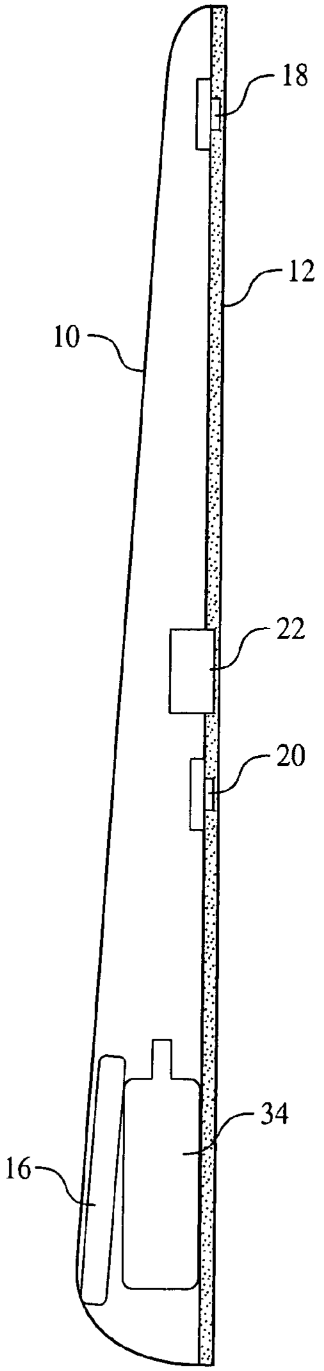
FIG. 4A shows a side view of a foot massaging device according to another embodiment of the invention.
Figure 4B:
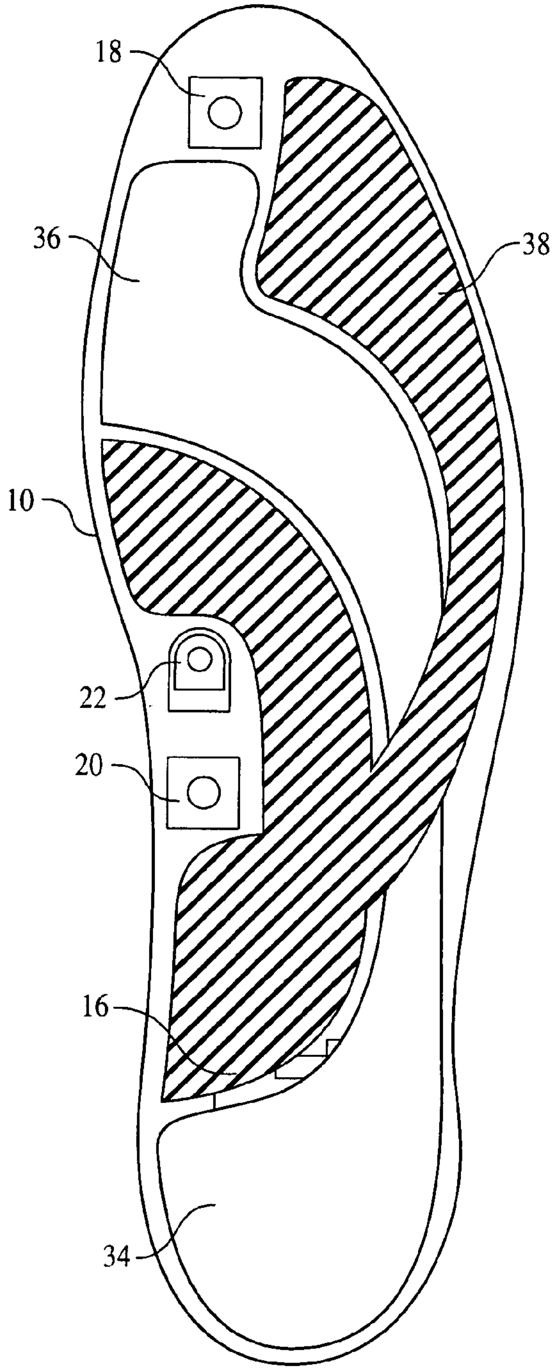
FIG. 4B shows a top view of the embodiment shown in FIG. 4A.
Figure 4C:
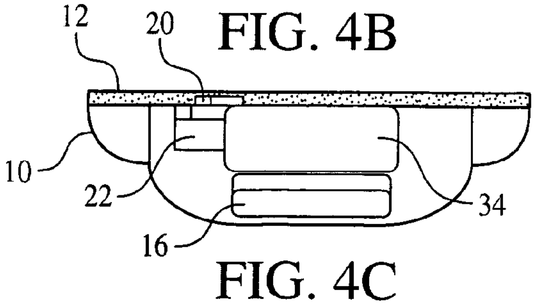
FIG. 4C shows a rear view of the embodiment shown in FIGS. 4A and 4B.
Figure 5A:
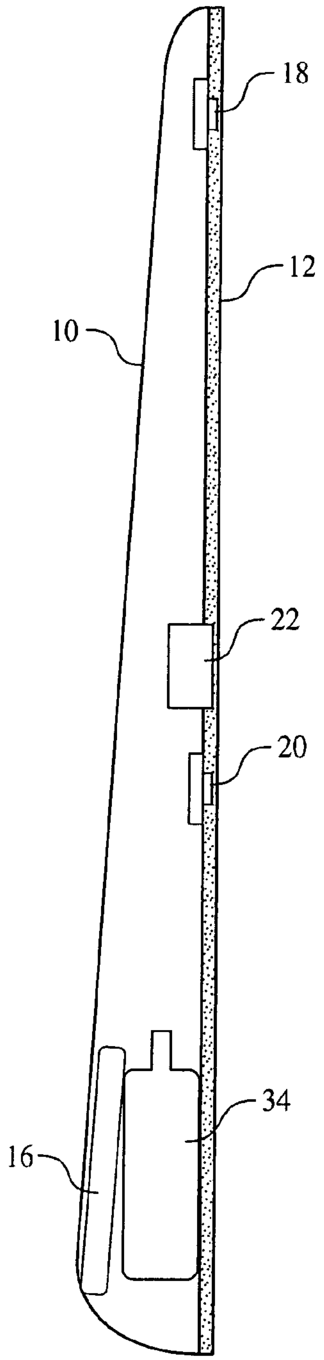
FIG. 5A shows a side view of a foot massaging device according to another embodiment of the invention.
Figure 5B:
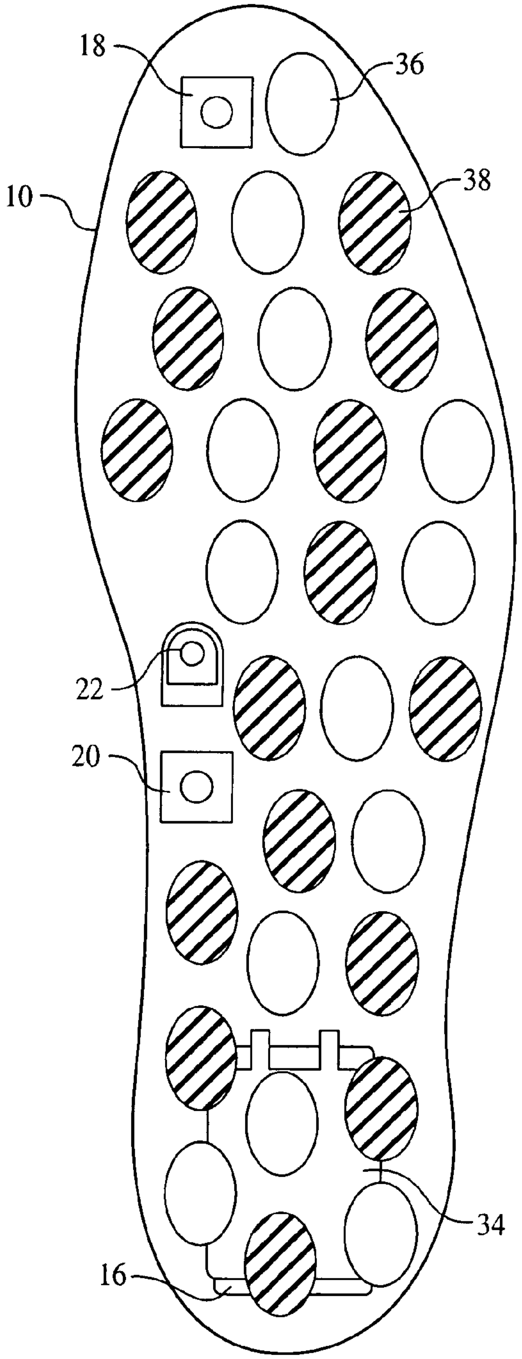
FIG. 5B shows a top view of the embodiment shown in FIG. 5A.
Figure 5C:
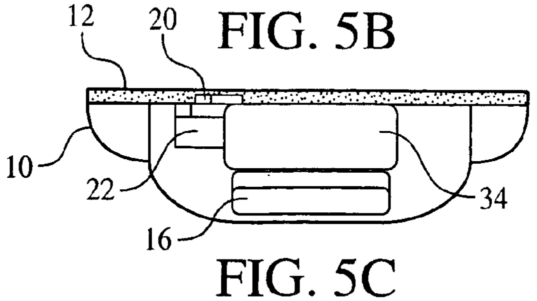
FIG. 5C shows a rear view of the embodiment shown in FIGS. 5A and 5B.

FIGS. 4 and 5 show alternate embodiments of a foot massaging device according to the invention. In these embodiments, a pump 34 is disposed in innersole 10. Preferably pump 34 is disposed in a cavity provided in innersole 10 and has a small profile. Pump 34 may be an electric pump powered by rechargeable battery 16 which is coupled to the pump with appropriate wiring or other electrical connections. One or more switches 18, 20 are coupled to rechargeable battery 16 and pump 34 for selectively powering pump 34 in manner similar to that described herein for motor 14.

A plurality of inflatable bladders 36, 38 are disposed within innersole 10. Each of the inflatable bladders 36, 38 are coupled to pump 34. When pump 34 is powered, inflatable bladders 36, 38 are inflated to produce a massaging effect on the bottom of a user's foot.

Inflatable bladders 36, 38 may be inflated with air or with a liquid. Preferably, inflatable bladders include a first inflatable bladder or first set of inflatable bladders 36 and a second inflatable bladder or second set of inflatable bladders 38, wherein the first inflatable bladder or first set of inflatable bladders 36 and the second inflatable bladder or second set of inflatable bladders 38 are alternately inflated.

Figure 8A:
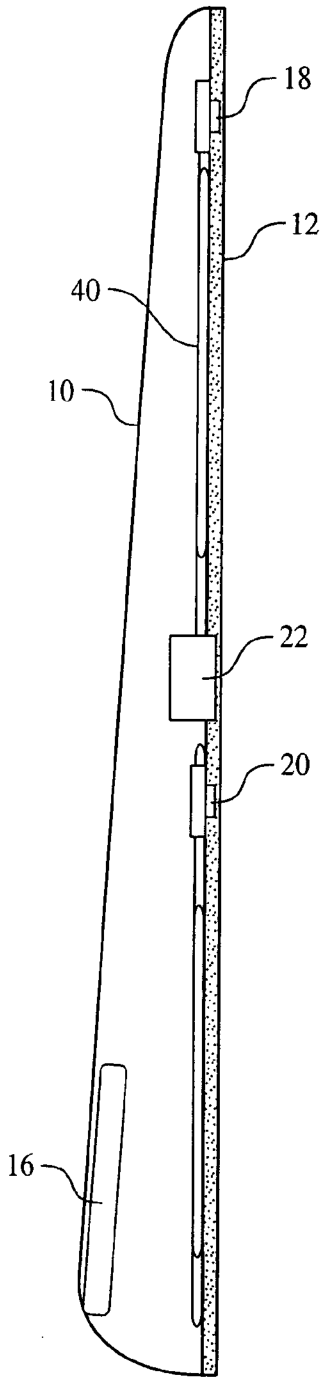
FIG. 8A shows a side view of a foot massaging device according to another embodiment of the invention.
Figure 8B:
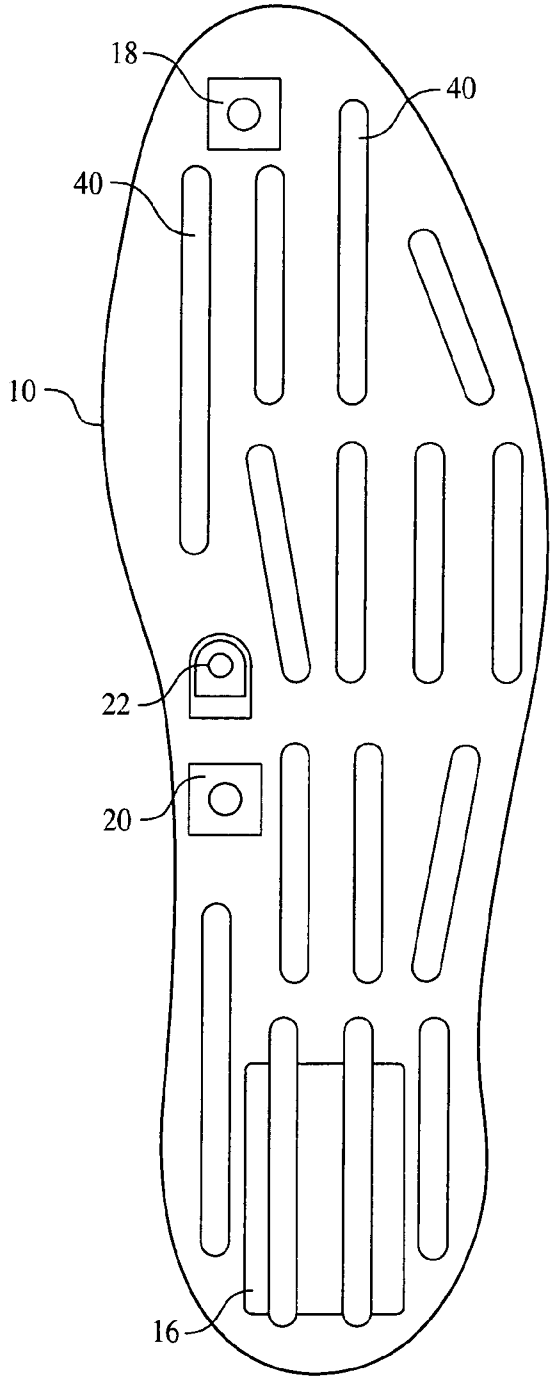
FIG. 8B shows a top view of the embodiment shown in FIG. 8A.
Figure 8C:
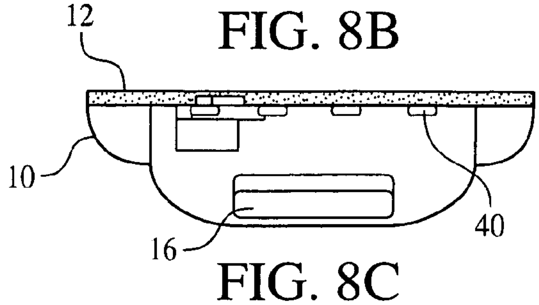
FIG. 8C shows a rear view of the embodiment shown in FIGS. 8A and 8B.

For example, inflatable bladders may be arranged as two discrete inflatable bladders as shown in FIG. 4B, wherein a first inflatable bladder 36 extends to a heel portion of innersole 10 and a second inflatable bladder 38 extends to a toe portion of innersole 10. Pump 34 may inflate and deflate each of inflatable bladders 36, 38 sequentially, in turn to produce an effective massaging action. Inflatable bladders may also be arranged as shown in FIG. 5B, wherein a plurality of first inflatable bladders 36 and a plurality of second inflatable bladders are arranged in an alternating manner over a top surface of innersole 10. Pump 34 may inflate and deflate each set of inflatable bladders 36, 38 sequentially, in turn to produce an effective massaging action FIG. 8 shows an alternate embodiment of a foot massaging device according to the invention. In this embodiment, a plurality of expanding and contracting bladders 40 are disposed in innersole 10. A plurality of artificial muscles are provided, each of the plurality of artificial muscles disposed in a cavity within a respective bladder 40. The artificial muscles expand and contract in response to an electrical current applied to the artificial muscles. Rechargeable battery 16 is coupled to the artificial muscles, for example with appropriate wiring or other electrical connections and supplies the electrical current to the artificial muscles.

When the electrical current is applied to the artificial muscles, the artificial muscles expand and contract within the bladders to produce a massaging effect on the bottom of a user's foot.

Accordingly, while several embodiments of the present invention have been shown and described, it is obvious that many changes and modifications may be made thereunto without departing from the spirit and scope of the invention.

What is claimed is:

1. A foot massaging device comprising:

a) an innersole for removably inserting in an article of footwear, said innersole comprising a flexible material;

b) a thin layer of material disposed over an upper surface of said innersole;

c) a motor disposed in a cavity provided in said innersole;

d) a rechargeable battery for powering said motor, said rechargeable battery disposed in said innersole and coupled to said motor;

e) a switch coupled to said rechargeable battery and to said motor for selectively powering said motor;

f) a charging port coupled to said rechargeable battery for coupling to a charger for charging said rechargeable battery;

g) a cam coupled to said motor;

h) a plurality of rails coupled to said cam, said plurality of rails being movable within channels provided in said innersole; and i) a plurality of spaced-apart rollers disposed on each of said plurality of rails;

wherein when said motor is powered, said cam is rotated causing said plurality of rails to move in a reciprocating manner, moving said plurality of rollers back and forth to produce a massaging effect on the bottom of a user's foot.

2. The foot massaging device according to claim 1, wherein said switch is positioned on an upper front surface of said innersole for actuating with a user's big toe when said innersole is disposed in the article of footwear.

3. The foot massaging device according to claim 1, further comprising a charger for charging said rechargeable battery, wherein said charger comprises two leads for simultaneously charging a pair of the foot massage devices while each of the pair of the foot massage devices is disposed in a respective article of footwear belonging to a pair of footwear.

4. A foot massaging device comprising:

a) an innersole for removably inserting in an article of footwear, said innersole comprising a flexible material;

b) a thin layer of material disposed over an upper surface of said innersole;

c) a pump disposed in a cavity disposed in said innersole;

d) a rechargeable battery for powering said pump, said rechargeable battery disposed in said innersole and coupled to said pump;

e) a switch coupled to said rechargeable battery and to said pump for selectively powering said pump;

f) a charging port coupled to said rechargeable battery for coupling to a charger for charging said rechargeable battery; and g) a plurality of inflatable bladders disposed within said innersole, each of said inflatable bladders coupled to said pump;

wherein when said pump is powered, said inflatable bladders are inflated to produce a massaging effect on the bottom of a user's foot.

5. The foot massaging device according to claim 4, wherein said switch is positioned on an upper front surface of said innersole for actuating with a user's big toe when said innersole is disposed in the article of footwear.

6. The foot massaging device according to claim 4, further comprising a charger for charging said rechargeable battery, wherein said charger comprises two leads for simultaneously charging a pair of the foot massage devices while each of the pair of the foot massage devices is disposed in a respective article of footwear belonging to a pair of footwear.

7. The foot massaging device according to claim 4, wherein said inflatable bladders are inflated with air.

8. The foot massaging device according to claim 4, wherein said inflatable bladders are inflated with a liquid.

9. The foot massaging device according to claim 4, wherein said plurality of bladders comprises a first bladder and a second bladder, wherein said first bladder and said second bladder are alternately inflated.

10. A foot massaging device comprising:

a) an innersole for removably inserting in an article of footwear, said innersole comprising a flexible material;

b) a thin layer of material disposed over an upper surface of said innersole;

c) a plurality of expanding and contracting bladders disposed in said innersole;

d) a plurality of artificial muscles, each of said plurality of artificial muscles disposed in a cavity within a respective bladder of said plurality of bladders; wherein said plurality of artificial muscles expand and contract in response to an electrical current applied thereto;

e) a rechargeable battery for applying the electrical current to said plurality of artificial muscles, said rechargeable battery disposed in said innersole and coupled to said artificial muscles;

f) a switch coupled to said rechargeable battery and to said artificial muscles for selectively applying the electrical current to said artificial muscles; and g) a charging port coupled to said rechargeable battery for coupling to a charger for charging said rechargeable battery;

wherein when the electrical current is applied to said artificial muscles, said artificial muscles expand and contract within said bladders to produce a massaging effect on the bottom of a user's foot.

11. The foot massaging device according to claim 10, wherein said switch is positioned on an upper front surface of said innersole for actuating with a user's big toe when said innersole is disposed in the article of footwear.

12. The foot massaging device according to claim 10, further comprising a charger for charging said rechargeable battery, wherein said charger comprises two leads for simultaneously charging a pair of the foot massage devices while each of the pair of the foot massage devices is disposed in a respective article of footwear belonging to a pair of footwear.

13. A foot massaging device comprising:

a) an innersole for removably inserting in an article of footwear, said innersole comprising a flexible material;

b) a thin layer of material disposed over an upper surface of said innersole;

c) a motor disposed in a cavity provided in said innersole;

d) a rechargeable battery for powering said motor, said rechargeable battery disposed in said innersole and coupled to said motor;

e) a switch coupled to said rechargeable battery and to said motor for selectively powering said motor;

f) a charging port coupled to said rechargeable battery for coupling to a charger for charging said rechargeable battery;

g) a cam coupled to said motor;

h) a plurality of rails coupled to said cam, said plurality of rails being movable within channels provided in said innersole; each of said plurality of rails comprising a plurality of teeth; and i) a plurality of spaced-apart pivoting rocker members disposed over said rails, each of said rocker members having a lever for engaging at least one of said plurality of teeth;

wherein when said motor is powered, said cam is rotated causing said plurality of rails to move in a reciprocating manner, and said teeth contact said levers causing said plurality of rocker members to pivot, producing a massaging effect on the bottom of a user's foot.

14. The foot massaging device according to claim 13, wherein said switch is positioned on an upper front surface of said innersole for actuating with a user's big toe when said innersole is disposed in the article of footwear.

15. The foot massaging device according to claim 4, further comprising a charger for charging said rechargeable battery, wherein said charger comprises two leads for simultaneously charging a pair of the foot massage devices while each of the pair of the foot massage devices is disposed in a respective article of footwear belonging to a pair of footwear.

* * * * *